United States Patent
Palmer et al.

(10) Patent No.: US 9,877,837 B2
(45) Date of Patent: Jan. 30, 2018

(54) DEVICES FOR ENHANCING THE FATIGUE AND MECHANICAL PROPERTIES OF BONE CEMENT AND OTHER BIOMATERIALS

(71) Applicant: MX ORTHOPEDICS, CORP., Lexington, MA (US)

(72) Inventors: Matthew Palmer, Cambridge, MA (US); Matthew Fonte, Concord, MA (US); Robert Devaney, Auburndale, MA (US)

(73) Assignee: ARTHREX, INC., Naples, FL (US)

( * ) Notice: Subject to any disclaimer, the term of this patent is extended or adjusted under 35 U.S.C. 154(b) by 0 days.

(21) Appl. No.: 15/266,003

(22) Filed: Sep. 15, 2016

(65) Prior Publication Data

US 2017/0071742 A1  Mar. 16, 2017

Related U.S. Application Data

(60) Provisional application No. 62/218,748, filed on Sep. 15, 2015.

(51) Int. Cl.
| | | |
|---|---|---|
| A61F 2/28 | (2006.01) |
| C01B 25/32 | (2006.01) |
| A61L 27/06 | (2006.01) |
| A61L 27/16 | (2006.01) |
| A61L 27/12 | (2006.01) |
| A61L 24/02 | (2006.01) |
| A61B 17/88 | (2006.01) |

(52) U.S. Cl.
CPC ........ *A61F 2/2846* (2013.01); *A61B 17/8805* (2013.01); *A61L 24/02* (2013.01); *A61L 27/06* (2013.01); *A61L 27/12* (2013.01); *A61L 27/16* (2013.01); *C01B 25/32* (2013.01); *A61F 2210/0071* (2013.01); *A61F 2210/0076* (2013.01); *A61F 2310/00023* (2013.01); *A61F 2310/00353* (2013.01); *A61L 2400/16* (2013.01)

(58) Field of Classification Search
CPC ..................... A61F 2/2846; A61F 2310/00353
See application file for complete search history.

(56) References Cited

U.S. PATENT DOCUMENTS

| | | | | |
|---|---|---|---|---|
| 6,827,743 B2 * | 12/2004 | Eisermann | ............. | A61B 17/68 623/23.54 |
| 2011/0137418 A1 * | 6/2011 | O'Neil | ....... | A61F 2/28 623/16.11 |
| 2013/0218288 A1 * | 8/2013 | Fonte | ....... | A61L 27/56 623/23.5 |

* cited by examiner

*Primary Examiner* — Brian Dukert
(74) *Attorney, Agent, or Firm* — Carlson, Gaskey & Olds

(57) ABSTRACT

A device includes a bone cement or a biomaterial and a mesh structure impregnated with the bone cement or the biomaterial. The mesh structure reinforces the bone cement or the biomaterial and reinforces the material's fatigue properties. The mesh structure may be made of a shape memory alloy.

17 Claims, 3 Drawing Sheets

DEVICES FOR ENHANCING THE FATIGUE AND MECHANICAL PROPERTIES OF BONE CEMENT AND OTHER BIOMATERIALS

CROSS-REFERENCE TO RELATED APPLICATIONS

This application claims priority to U.S. Provisional Application No. 62/218,748, filed on Sep. 15, 2015, the disclosure of which is incorporated herein by reference in its entirety.

TECHNICAL FIELD

The present disclosure relates to devices and methods for enhancing the fatigue and other mechanical properties of polymethyl methacrylate (PMMA, bone cement) and other structural biomaterials such as calcium phosphate, tri-calcium phosphate, hydroxyapatite, and other biocompatible materials. The disclosure finds particular utility in the field of orthopedics. While the disclosure has utility throughout the body, its utility will be illustrated herein in the context of bone cement with enhanced fatigue and mechanical properties for cementing joint prosthetics into bone and calcium phosphate with enhanced fatigue and mechanical properties that is manufactured into weight bearing implants, such as spinal cages, and osteotomy wedge implants.

BACKGROUND

In the field of orthopedic surgery, polymethyl methacrylate (PMMA) is widely used as a cement to anchor artificial joints to bone. The PMMA fills the free spaces between the prosthesis and the bone. A prosthesis fixed with bone cement offers very high primary stability combined with fast remobilization of patients. This is because the cemented-in prosthesis can be fully loaded very soon after the operation, since PMMA achieves the majority of its strength within the first 24 hours. Additionally, bone cement formulations can be modified to include active substances such as antibiotics. The antibiotics are locally released and act against bacteria precisely at the site where they are needed.

PMMA is supplied as a powder with liquid methyl methacrylate (MMA). When these two are combined, a dough is formed which can be used as a grouting agent to affix implants and remodel lost bone. While sticky, it does not bond to either the bone or the implant. Instead, it fills the spaces between the prosthesis and the bone preventing motion.

A disadvantage of bone cement is that the polymerization reaction is highly exothermic, and the bone cement can heat up to 82.5° C. while setting. This can cause thermal necrosis of neighboring tissue. Additionally, PMMA has been shown to cause stress shielding. PMMA has a Young's modulus between 1.8 and 3.1 GPa, which is lower than that of natural cortical bone. This causes the stresses to be loaded into the cement and thus the bone no longer receives the mechanical stimuli to continue bone remodeling. This can cause bone resorption to occur.

Mechanically, PMMA, when fully hardened, is strong but brittle. It is very strong in compression and resists creep; however, it has low ductility and a high susceptibility to stress crazing. This leads to larger cracks, relative motion between the implant and the bone, and eventual failure requiring the implant and PMMA to be removed and replaced. Thus there exists a clinical need for PMMA with improved fatigue resistance and enhanced mechanical properties.

In the field of orthopedics, hydroxyapatite, calcium phosphate, and tricalcium phosphate are widely used as a fillers to replace bone or as a coating to promote bone ingrowth. The material is remodeled by bone cells leading to healing. These biomaterials are, however, not load bearing. Screws, plates, and other hardware are used to transmit the load and the hydroxyapatite, calcium phosphate, and tricalcium phosphate is used as a space filler.

It has been found that these materials suffer from low crack resistance and low fatigue durability. This precludes them from being used as load bearing materials. Thus there is a clinical need for enhancing the fatigue properties and mechanical properties of these biomaterials in order to use them as structural biomaterials.

SUMMARY

This disclosure relates to devices and methods for enhancing the fatigue properties and other mechanical properties of bone cements and other structural biomaterials. A mesh device may be impregnated with a bone cement or a biomaterial to improve the fatigue life of the bone cement or biomaterial.

A device according to an exemplary aspect of this disclosure includes, inter alia, a mesh structure impregnated with a bone cement or a biomaterial. The mesh structure includes a shape memory alloy.

A device according to another exemplary aspect of this disclosure includes, inter alia, a bone cement or a biomaterial reinforced with a porous fabric mesh. The porous fabric mesh is manufactured from superelastic Nitinol wire.

A surgical method according to an exemplary aspect of this disclosure includes, inter alia, inserting a mesh device into a bone canal, and drying, curing, or sintering the mesh structure.

DETAILED DESCRIPTION

This disclosure relates to devices and methods for improving the fatigue life of bone cements and biomaterials. A mesh structure, such as a metallic fiber mesh, can be impregnated with a bone cement or other biomaterials much like rebar in cement. The mesh structure reinforces the material and enhances the material's fatigue properties.

A device according to an exemplary aspect of this disclosure includes, inter alia, a mesh structure impregnated with a bone cement or a biomaterial. The mesh structure includes a shape memory alloy.

In a further embodiment, a shape memory alloy is Nitinol.

In a further embodiment, a biomaterial is polymethyl methacrylate (PMMA).

In a further embodiment, a bone cement is calcium phosphate.

In a further embodiment, a bone cement is tricalcium phosphate.

In a further embodiment, a bone cement is hydroxyapatite.

In a further embodiment, a mesh structure is a three-dimensional spacer fabric.

In a further embodiment, a mesh structure is configured to reinforce a bone cement or a biomaterial.

In a further embodiment, a mesh structure is impregnated with a bone cement or a biomaterial prior to polymerization, drying, curing, or sintering.

In a further embodiment, a mesh structure includes a top layer, a bottom layer, and a plurality of connecting layers that connect between the top layer and the bottom layer.

A device according to another exemplary aspect of this disclosure includes, inter alia, a bone cement or a biomaterial reinforced with a porous fabric mesh. The porous fabric mesh is manufactured from superelastic Nitinol wire.

In a further embodiment, a biomaterial is polymethyl methacrylate (PMMA).

In a further embodiment, a biomaterial is calcium phosphate, tricalcium phosphate, or hydroxyapatite.

A surgical method according to an exemplary aspect of this disclosure includes, inter alia, inserting a mesh device into a bone canal, and drying, curing, or sintering the mesh structure.

In a further embodiment, an implant is inserted into a bone canal after inserting a device into the bone hole.

In a further embodiment, a hip implant is inserted into a femoral canal.

In a further embodiment, a mesh structure is expanded into an implant in response to an exothermic polymerization reaction.

In a further embodiment, additional bone cement or additional biomaterial is inserted into a gap between a mesh structure and an implant.

Figure 1:
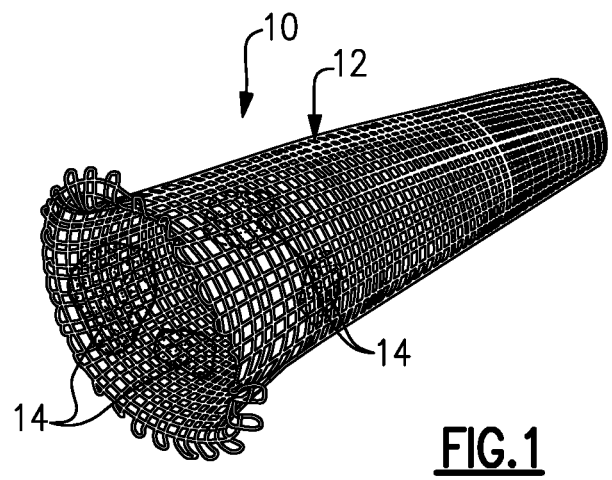
FIG. 1 illustrates a device according to an embodiment of this disclosure.

FIG. 1 illustrates a device 10 according to an exemplary embodiment of this disclosure. The device 10 include a mesh structure 12 and a material 14. The mesh structure 12 can be impregnated with the material 14 (shown schematically). The material 14 may be a bone cement or any other biomaterial. The mesh structure 12 reinforces the material 14 and enhances the fatigue properties of the material 14.

The device 10 of FIG. 1 is shaped into a sleeve. However, other shapes are contemplated within the scope of this disclosure.

In another embodiment, a highly porous fabric mesh can be impregnated with PMMA prior to polymerization, and then pressed into a bone canal awaiting an implant, such as a hip implant. Additional PMMA can be used as a grout to fill any gaps that remain. The porous fabric mesh acts as a rebar structure. The mesh carries the tensile loads and provides a means to more evenly distribute stress and confer resistance to concentrated loads. The mesh's tensile properties and stiffness spread loads more evenly over wider areas.

In yet another embodiment, a highly porous fabric mesh can be impregnated with calcium phosphate, tricalcium phosphate, hydroxyapatite or other biologic prior to a drying/sintering of the material. The porous fabric mesh acts as a rebar structure. The mesh carries the tensile loads and provides a means of more evenly distributing stress and confers resistance to concentrated loads. The mesh's tensile properties and stiffness spread loads more evenly over wider areas.

The mesh material can be different structures and made from different materials. The mesh can be largely two dimensional, or more three dimensional like a porous metal foam. The mesh can be made from metals, polymers, or other organic/inorganic fibers. The mesh can be manufactured using knitting, weaving, felting, or braiding techniques.

Figure 2:
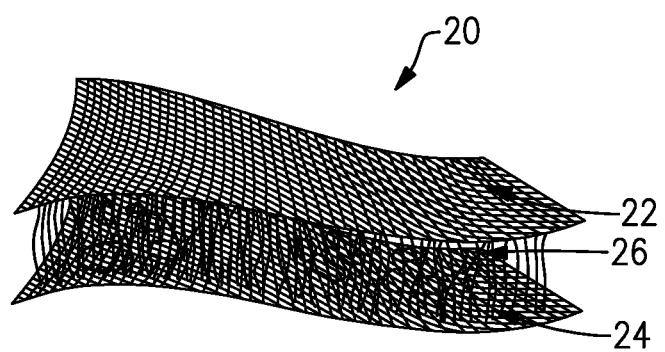
FIG. 2 illustrates an exemplary mesh structure according to an embodiment of this disclosure.

One structure that finds particular utility as a material to enhance the mechanical properties of bone cement, calcium phosphate, tricalcium phosphate, and hydroxyapatite is a three dimensional spacer fabric 20 (shown in FIG. 2) manufactured from superelastic Nitinol wire. A spacer fabric is a woven or knit three dimensional fabric that has a top face 22, a bottom face 24, and a plurality of generally perpendicular connecting fibers 26.

Figure 3:
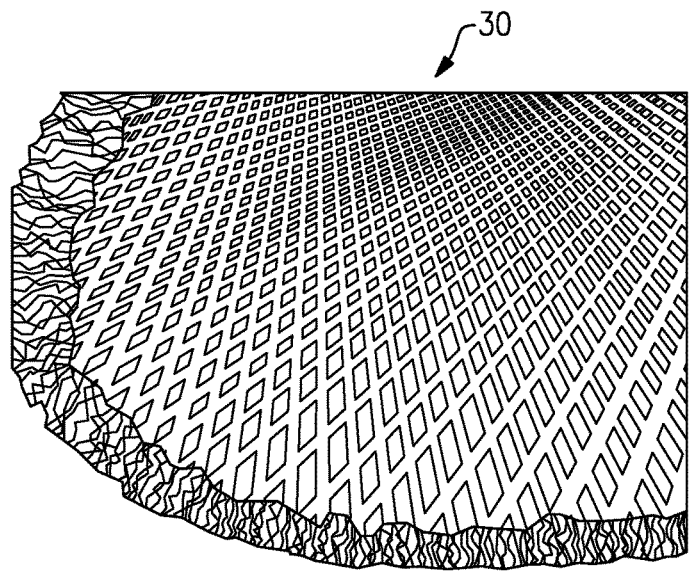
FIG. 3 illustrates a mesh structure according to another embodiment of this disclosure.
Figure 4:
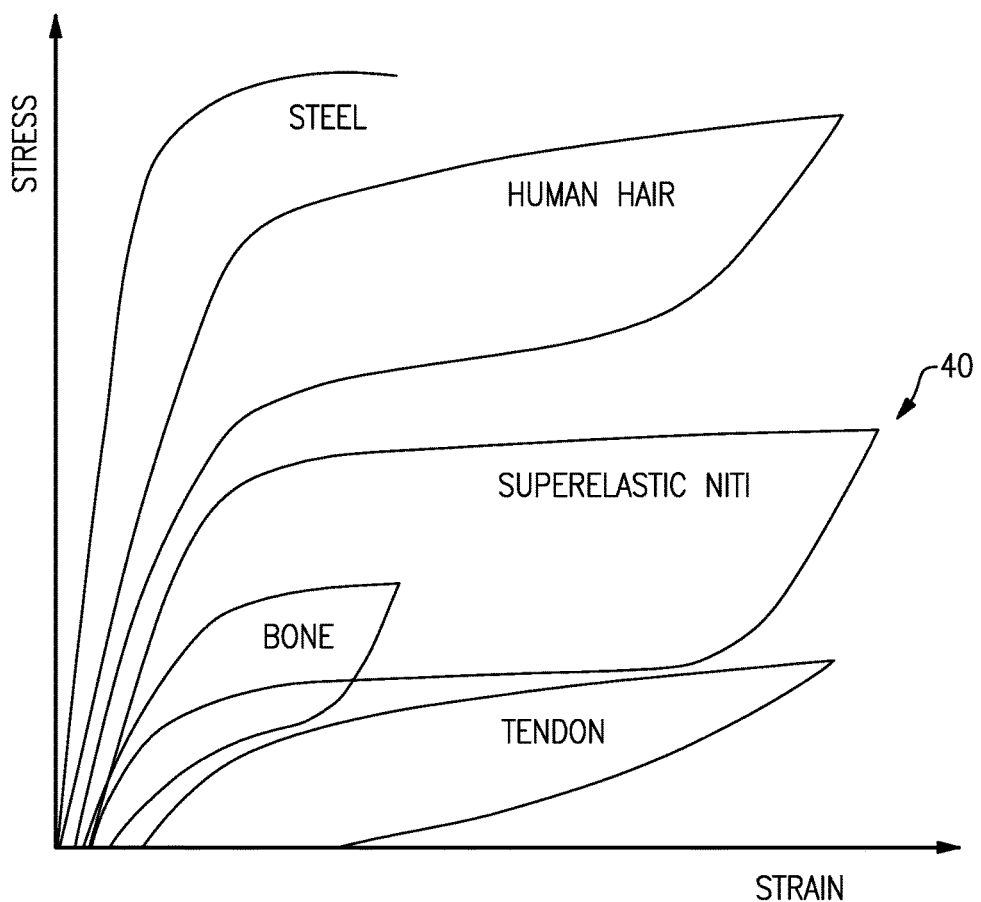
FIG. 4 is a schematic showing the hysteresis curve for the loading and unloading of a Nitinol structure.

While spacer fabrics are often manufactured from polymers such as nylon or polyester, one can manufacture a spacer fabric from metallic wire. In particular, one can manufacture the spacer fabric from Nitinol wire. An exemplary Nitinol spacer fabric construct 30 is illustrated in FIG. 3. Nitinol is a superelastic, shape memory alloy. The superelastic nature of Nitinol allows the spacer fabric construct 30 to be crush resistant. This is beneficial when massaging the materials into the pores of the fabric. Additionally, Nitinol exhibits a loading and unloading profile very similar to bone (see, e.g., plot 40 of FIG. 4), thus assisting in load sharing between the reinforced material and the bone.

Thus, the Nitinol can be used to enhance the mechanical properties of the PMMA, calcium phosphate, tricalcium phosphate, and hydroxyapatite. Nitinol can either be in its martensitic (cold) phase, or its austenitic (warm) phase. It is stronger and stiffer in its warm phase.

Figure 5:
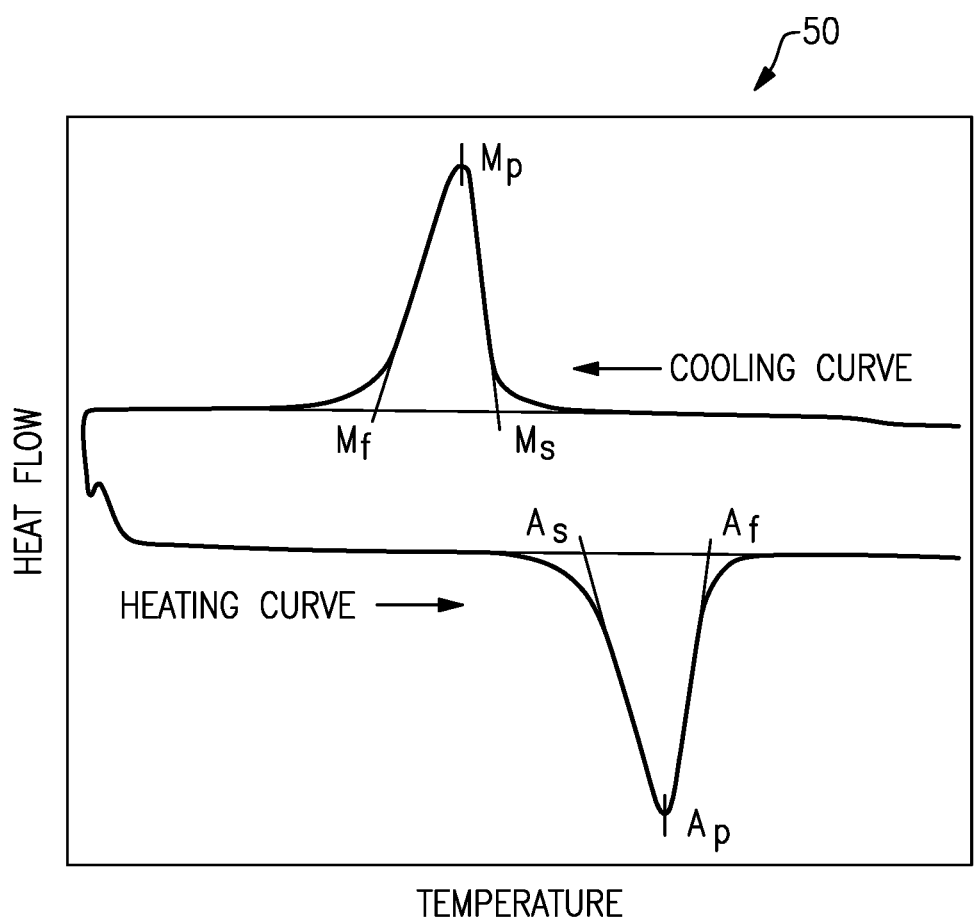
FIG. 5 is a schematic showing a differential scanning calorimeter (DSC) curve of a Nitinol structure.

For bone cement applications, Nitinol can be programmed to change shape when warmed from its martensitic to austenitic phase (see, e.g., plot 50 of FIG. 5). Thus, the Nitinol spacer fabric can be manufactured in its martensitic phase. This makes it easier for the surgeon to bend to fit the anatomy. An implant, such as a hip implant, can then be pressed into the femoral canal. As the exothermic polymerization reaction occurs, the Nitinol will warm to its Austentic phase and attempt to revert to its previously programmed shape. This shape can be an expanded form of the spacer fabric. Thus as the polymerization powers the change from martensite to austenite, the spacer fabric can expand and help more firmly lock the implant into the PMMA, and also push the PMMA into all the crevices around the bone. Additionally, the transformation from martensite to austenite is endothermic. Thus, the Nitinol mesh would absorb some of the heat energy released by the polymerization reaction. This can help reduce the ultimate temperature the bone experiences and limit local tissue necrosis.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A surgical method, comprising:
   inserting a device including a mesh structure impregnated with a bone cement or a biomaterial into a bone canal, wherein the mesh structure comprises a shape memory alloy;

drying, curing, or sintering the mesh structure;
inserting an implant into the bone canal after inserting the device; and
in response to an exothermic polymerization reaction:
 expanding the mesh structure into the implant.

2. The method as recited in claim 1, wherein the bone canal is a femoral canal and the implant is a hip implant.

3. The method as recited in claim 1, wherein the shape memory alloy is Nitinol.

4. The method as recited in claim 1, wherein the biomaterial is polymethyl methacrylate (PMMA).

5. The method as recited in claim 1, wherein the bone cement is calcium phosphate.

6. The method as recited in claim 1, wherein the bone cement is tricalcium phosphate.

7. The method as recited in claim 1, wherein the bone cement is hydroxyapatite.

8. The method as recited in claim 1, wherein the mesh structure is a three-dimensional spacer fabric.

9. The method as recited in claim 1, wherein the device is shaped into a sleeve.

10. A surgical method, comprising:
 inserting a device including a mesh structure impregnated with a bone cement or a biomaterial into a bone canal, wherein the mesh structure comprises a shape memory alloy;
 drying, curing, or sintering the mesh structure;
 inserting an implant into the bone canal after inserting the device; and
 inserting additional bone cement or additional biomaterial into a gap between the mesh structure and the implant.

11. The method as recited in claim 10, wherein the shape memory alloy is Nitinol.

12. The method as recited in claim 10, wherein the biomaterial is polymethyl methacrylate (PMMA).

13. The method as recited in claim 10, wherein the bone cement is calcium phosphate.

14. The method as recited in claim 10, wherein the bone cement is tricalcium phosphate.

15. The method as recited in claim 10, wherein the bone cement is hydroxyapatite.

16. The method as recited in claim 10, wherein the mesh structure is a three-dimensional spacer fabric.

17. The method as recited in claim 10, wherein the device is shaped into a sleeve.

\* \* \* \* \*